United States Patent [19]
Moore et al.

[11] 3,950,229
[45] Apr. 13, 1976

[54] PURIFICATION OF ADIPONITRILE

[75] Inventors: Colin Moore; Michael Joseph Thornton, both of Stockton-on-Tees, England

[73] Assignee: Imperial Chemical Industries Limited, London, England

[22] Filed: Apr. 22, 1974

[21] Appl. No.: 463,128

[30] Foreign Application Priority Data
Apr. 24, 1973 United Kingdom............... 19272/73

[52] U.S. Cl............... 203/38; 203/59; 260/465.8 R; 260/465.2; 260/464; 260/465.4
[51] Int. Cl.²............................................ B01D 3/34
[58] Field of Search....... 260/465.8, 465.2, 465.8 R; 203/38, 57, 59, 60

[56] References Cited
UNITED STATES PATENTS

| | | | |
|---|---|---|---|
| 2,570,794 | 10/1951 | Grigsby et al................ | 260/465.8 R |
| 2,748,065 | 5/1956 | Trieschmann et al................ | 203/38 |
| 2,768,132 | 10/1956 | Halliwell...................... | 260/465.8 R |
| 2,803,643 | 8/1957 | Halliwell...................... | 260/465.8 R |
| 3,152,186 | 10/1964 | Campbell et al......... | 260/465.8 R X |
| 3,177,242 | 4/1965 | Adam et al................... | 260/465.8 R |
| 3,350,281 | 10/1967 | Romani et al............ | 260/465.8 R X |
| 3,429,783 | 2/1969 | Campbell et al.................. | 203/38 X |
| 3,853,947 | 12/1974 | Golser et al.................. | 260/465.8 R |

Primary Examiner—Joseph P. Brust
Attorney, Agent, or Firm—Cushman, Darby & Cushman

[57] ABSTRACT

Adiponitrile is separated from impurities of boiling point close to that of adiponitrile, especially 5-cyanovaleric acid and 2-cyanocyclopenten-(1)-ylamine, by reacting the impurities with a primary or secondary amine to give compounds of higher boiling point and then fractionally distilling to separate the adiponitrile.

6 Claims, No Drawings

PURIFICATION OF ADIPONITRILE

THIS INVENTION relates to the purification of adiponitrile, and more especially to the separation of adiponitrile from impurities having closely similar boiling points to that of adiponitrile.

Adiponitrile is an important intermediate in the sequence of chemical operations leading to certain polyamides known as the nylons. Thus hydrogenation of adiponitrile gives hexamethylene diamine which on poly-condensation with dicarboxylic acids gives nylon polymers, for example polycondensation with adipic acid gives polyhexamethylene adipamide (nylon 6,6) which is used in the manufacture of mouldings and for melt spinning into textile yarns. For such purposes, and particularly when yarns are to be manufactured, it is important that the hexamethylene diamine be as pure as possible since even very small amounts of impurities can have an adverse effect on the final polyamide, especially on yarn properties. This means that the precursor adiponitrile must also be as pure as possible since impurities carried through with the adiponitrile may form impurities in the hexamethylene diamine which are very difficult to remove.

Separation of impurities from adiponitrile and from hexamethylene diamine is usually effected by fractional distillation. In the case of impurities having boiling points close to that of adiponitrile or hexamethylene diamine as the case may be, separation is difficult and requires the use of elaborate fractionating columns with a large number of theoretical plates, and even then separation may not be as complete as desired. A particular impurity of this kind in adiponitrile, especially in adiponitrile manufactured by the dehydrative amination of adipic acid, is 2-cyanocyclopentene-1-ylamine (also called 1-amino-2-cyanocyclopentene) which at a pressure of 10 mm. mercury has a boiling point of 148°C compared with a boiling point of 155°C for adiponitrile. On reduction of adiponitrile containing such impurity to hexamethylene diamine the 2-cyanocyclopenten-(1)-ylamine is itself reduced to 2-aminoethylcyclopentylamine which is also very close in boiling point to hexamethylene diamine and hence difficult to sepatate therefrom. Moreover, 2-aminomethylcyclopentylamine in hexamethylene diamine which is used in the manufacture of nylon 6,6 has an adverse effect on yarn spun therefrom. Accordingly every effort is made to reduce the proportion of 2-cyanocyclopenten-(1)-ylamine in adiponitrile to a minimum. As already mentioned separation by fraction distillation is difficult owing to the closeness of the boiling points. Moreover the melting point of 2-aminocyclopenten-(1)-ylamine, at 148°C, is very close to its boiling point at 10 mm. pressure leading to the difficulty of blockages in condensers and transfer lines unless a substantial amount of adiponitrile is also removed with the impurity, which, of course, is wasteful of adiponitrile.

Another impurity in adiponitrile which is difficult to remove to the desired level by fractional distillation is 5-cyanovaleric acid (b.pt. 175°C/10 mm. compared with a b.pt. of 155°C/10 mm. for adiponitrile). It is desirable to reduce the content of this impurity as much as possible since it may have a corrosive effect on equipment containing ferrous metals.

We have now found that the separation of adiponitrile from 2-cyanocyclopenten-(1)ylamine and/or 5-cyanovaleric acid in mixtures of such impurity with adiponitrile is facilitated if the impure adiponitrile is contacted with a primary or secondary amine under conditions such that the impurity reacts with the said amine to give a compound of higher boiling point, and then fractionally distilling to separate the adiponitrile. The amine should chosen so as to be significantly different in boiling point from adiponitrile. Such a method is obviously applicable to other impurities having boiling points close to that of adiponitrile which react with the said amines to give compounds a higher boiling point.

Accordingly our invention provides a process for separating adiponitrile from amine-reactable impurities having boiling points close to that of adiponitrile which process comprises contacting the impure adiponitrile with a primary or secondary amine having a boiling point significantly different from that of adiponitrile so that the said impurities react with the said amine to give compounds of higher boiling point, and fractionally distilling to separate adiponitrile from the resulting mixture.

By amine-reactable impurities having boiling points close to that of adiponitrile we mean in particular such impurities as differ in boiling point, at a given pressure, from adiponitrile by up to 20°C. Such impurities include in particular 5-cyanovaleric acid, and especially 2-cyanocyclopenten-(1)-ylamine. The primary or secondary amines with which the impure adiponitrile is contacted have boiling points significantly different from adiponitrile, in particular they differ from it in boiling point by more than 20°C, whether above or below.

Contacting the impure adiponitrile with the amine may take place over a wide range of conditions. The temperature of treatment may vary widely, for example from 0° to 250°C, although we prefer a temperature range of 75° to 200°C. Again the time of treatment may vary widely, depending to some extent, of course, on the temperature used, but times from a few minutes (say, 10 mins.) up to many hours (say, 48 hrs.) may be used. The amount of amine used depends on the amount of impurity it is desired to react therewith. Generally speaking the amount of amine used falls within the range of 0.1 to 10 times the weight of the impurity it is desired to react.

Among many primary or secondary amines which may be used we prefer aliphatic or cycloaliphatic amines or saturated heterocyclic amines. We also prefer amines having boiling points in excess of 100°C at atmospheric pressure.

Particularly suitable amines are hexamethylene diamine (b.pt. 80°C/10 mm), 1,2-diaminocyclohexane (b.pt. 70°C/10 mm) and bis(hexamethylene)triamine (b.pt. 190°C/10 mm). Particularly suitable also is the high boiling residue obtained from the distillation of hexamethylene diamine manufactured by hydrogenation of adiponitrile, which residue is a mixture of high boiling amines, principally bis-(hexamethylene)-triamine.

Treatment of impure adiponitrile with amines according to the process of our invention followed by fractional distillation enables the content of 2 cyanocyclopenten-(1)-ylamine and/or 5-cyanovaleric acid to be reduced compared with impure adiponitrile which has not been so treated.

The invention is illustrated but not limited by the following Examples in which the parts and percentages are by weight unless otherwise stated.

EXAMPLE 1

Comparative Example

500 Parts of dried, crude adiponitrile containing 0.50% of 2-cyanocyclopenten-(1)-ylamine and 0.87% of 5-cyanovaleric acid were distilled at 10 mm. mercury pressure. The distillate, 472 parts, contained 0.52% of 2-cyanocyclopenten-(1)-ylamine and 0.69% of 5-cyanovaleric acid.

EXAMPLE 2

To 500 parts of dried, crude adiponitrile containing 0.58% of 2-cyanocyclopenten-(1)-ylamine and 0.87% of 5-cyanovaleric acid was added 5 parts (1% by weight of the crude adiponitrile) of bis-(hexamethylene)-triamine. The mixture was heated at 110°C for 3 hours. It was then distilled at 10 mm. mercury pressure. The distillate, 480 parts, contained 0.03% of 2-cyanocyclopenten-(1)-ylamine and 0.29% of 5-cyanovaleric acid.

EXAMPLE 3

To 500 parts of dried, crude adiponitrile containing 0.52% of 2-cyanocyclopenten-(1)-ylamine and 0.87% of 5-cyanovaleric acid was added 5 parts (1% by weight of the crude adiponitrile) of hexamethylene diamine. The mixture was heated at 120°C for 3 hours. It was then distilled at 20 mm. pressure. The distillate, 465 parts, contained 0.02% of 2-cyanocyclopenten-(1)-ylamine and 0.13% of 5-cyanovaleric acid.

We claim:

1. A process for separating adiponitrile from 2-cyanocyclopenten-(1)-ylamine, 5-cyanovaleric acid, or both present as impurities in adiponitrile which comprises reacting said impurities with an amine having a boiling point in excess of 100°C at atmospheric pressure and differing in boiling point from adiponitrile at a given pressure by more than ±20°C, said amine being selected from the group consisting of hexamethylene diamine, 1,2-diaminocyclohexane, bis-hexamethylene triamine, and the high boiling residue obtained from the distillation of hexamethylene diamine manufactured by hydrogenation of adiponitrile, to give compounds of higher boiling point than adiponitrile, by contacting the impure adiponitrile with said amine in an amount of from 0.1 to 10 times the weight of said impurity at from 0° to 250°C for 10 minutes to 48 hours, and fractionally distilling to separate adiponitrile from the resulting mixture.

2. The process of claim 1 in which the impure adiponitrile is contacted with the amine at a temperature in the range of 75° to 200°C.

3. A process for separating adiponitrile from 2-cyanocyclopenten-(1)-ylamine, 5-cyanovaleric acid, or both present as impurities in adiponitrile manufactured by the dehydrative amination of adipic acid, which comprises reacting said impurities with an amine having a boiling point in excess of 100°C at atmospheric pressure and differing in boiling point from adiponitrile at a given pressure by more than ± 20°C, said amine being selected from the group consisting of a primary or secondary amine, to give compounds of higher boiling point than adiponitrile, by contacting the impure adiponitrile with said amine in an amount of from 0.1 to 10 times the weight of said impurity at from 0° to 250°C for 10 minutes to 48 hours, and fractionally distilling to separate adiponitrile from the resulting mixture.

4. The process of claim 3 in which the primary or secondary amine with which the impure adiponitrile is contacted is hexamethylene diamine, 1,2-diaminocyclohexane or bis-hexamethylene triamine.

5. The process of claim 3 in which the primary or secondary amine with which the impure adiponitrile is contacted is the high boiling residue obtained from the distillation of hexamethylene diamine manufactured by hydrogenation of adiponitrile.

6. The process of claim 3 in which the impure adiponitrile is contacted with the amine at a temperature in the range of 75° to 200°C.

* * * * *